(12) United States Patent
Zhao et al.

(10) Patent No.: US 6,903,110 B2
(45) Date of Patent: Jun. 7, 2005

(54) ANTIDEPRESSANT AZAHETEROCYCLYLMETHYL DERIVATIVES OF 7,8-DIHYDRO-6H-5-OXA-1-AZA-PHENANTHRENE

(75) Inventors: Rulin Zhao, Pennington, NJ (US); Megan Tran, Hoboken, NJ (US); Gary P. Stack, Ambler, PA (US); Richard E. Mewshaw, King of Prussia, PA (US)

(73) Assignee: Wyeth, Madison, NJ (US)

( * ) Notice: Subject to any disclaimer, the term of this patent is extended or adjusted under 35 U.S.C. 154(b) by 198 days.

(21) Appl. No.: 10/201,862

(22) Filed: Jul. 24, 2002

(65) Prior Publication Data

US 2003/0078268 A1 Apr. 24, 2003

Related U.S. Application Data

(60) Provisional application No. 60/307,667, filed on Jul. 25, 2001.

(51) Int. Cl.[7] ..................... C07D 491/04; A61K 31/44; A61P 25/24
(52) U.S. Cl. ......................... 514/291; 546/89
(58) Field of Search ............................. 546/89; 514/291

(56) References Cited

U.S. PATENT DOCUMENTS

| | | | |
|---|---|---|---|
| 5,318,988 A | 6/1994 | Schohe-Loop et al. | 514/458 |
| 5,371,094 A | 12/1994 | Heine et al. | 514/323 |
| 5,693,655 A | 12/1997 | Bottcher et al. | 514/323 |
| 5,741,789 A | 4/1998 | Hibschman et al. | 514/210 |
| 5,756,532 A | 5/1998 | Stack et al. | 514/411 |
| 5,869,490 A | 2/1999 | Stack | 514/255 |

FOREIGN PATENT DOCUMENTS

| | | |
|---|---|---|
| WO | WO 91/11435 | 8/1991 |
| WO | WO 99/11619 | 3/1999 |

OTHER PUBLICATIONS

Vaswani et al. Role of selective serotonin reuptake inhibitors in psychiatric disoders: a comprehensive review, Prog. Neuropsychopharmacol. Biol. Psychiatry 27: 85–102, 2003 (abstract).*

John E. Macor et al., J. Med. Chem., 1992, 3625–3632, 35.

Ethan W. Taylor et al., Mol. Pharm., 1988, 42–53, 34(1).

* cited by examiner

Primary Examiner—Mukund J. Shah
Assistant Examiner—Hong Liu
(74) Attorney, Agent, or Firm—Woodcock Washburn LLP

(57) ABSTRACT

Compounds of the formula useful for the treatment of such as depression (including but not limited to major depressive disorder, childhood depression and dysthymia), anxiety, panic disorder, post-traumatic stress disorder, premenstrual dysphoric disorder (also known as premenstrual syndrome), attention deficit disorder (with and without hyperactivity), obsessive compulsive disorder (including trichotillomania), social anxiety disorder, generalized anxiety disorder, obesity, eating disorders such as anorexia nervosa, bulimia nervosa, vasomotor flushing, cocaine and alcohol addition, sexual dysfunction (including premature ejaculation), and related illnesses.

26 Claims, No Drawings

ANTIDEPRESSANT AZAHETEROCYCLYLMETHYL DERIVATIVES OF 7,8-DIHYDRO-6H-5-OXA-1-AZA-PHENANTHRENE

This application claims priority from co-pending provisional application Ser. No. 60/307,667, filed on Jul. 25, 2001, the entire disclosure of which is hereby incorporated by reference.

BACKGROUND OF THE INVENTION

Major depressive disorder affects an estimated 340 million people worldwide. According to the World Health Organization, depression is the fourth greatest public health problem. If left untreated, the effects of depression can be devastating, robbing people of the energy or motivation to perform everyday activities and, in some cases, leading to suicide. Symptoms of the disorder include feelings of sadness or emptiness, lack of interest or pleasure in nearly all activities, and feelings of worthlessness or inappropriate guilt. In addition to the personal costs of depression, the disorder also results in more than $40 billion in annual costs in the United States alone, due to premature death, lost productivity, and absenteeism.

Selective serotonin reuptake inhibitors (SSRIs) have had significant success in treating depression and related illnesses and have become among the most prescribed drugs. They nonetheless have a slow onset of action, often taking several weeks to produce their full therapeutic effect. Furthermore, they are effective in fewer than two-thirds of patients.

SSRIs work by blocking the neuronal reuptake of serotonin, which tends to increase the concentration of serotonin in the synaptic space, and thus increase the activation of postsynaptic serotonin receptors. However, although a single dose of an SSRI can inhibit the neuronal serotonin transporter and thus would be expected to increase synaptic serotonin, long-term treatment is required before clinical improvement is achieved. It has been suggested that the SSRIs increase the serotonin levels in the vicinity of the serotonergic cell bodies and that the excess serotonin activates somatodendritic autoreceptors, 5-$HT_{1A}$ receptors, causing a decrease in serotonin release in major forebrain areas. This negative feedback limits the increment of synaptic serotonin that can be induced by antidepressants acutely. Over time, the somatodendritic autoreceptors become desensitiized, allowing the full effect of the SSRI to be expressed in the forebrain. This time period corresponds to the latency for the onset of antidepressant activity [Perez, V., et al., *The Lancet*, 349:1594–1597 (1997)].

A 5-$HT_{1A}$ agonist or partial agonist acts directly on postsynaptic serotonin receptors to increase serotonergic neurotransmission during the latency period for the SSRI effect. Accordingly, the 5-$HT_{1A}$ partial agonists buspirone and gepirone [Feiger, A., *Psychopharmacol. Bull.*, 32(4), 659–665 (1996), Wilcox, C., *Psychopharmacol. Bull.*, 32(3), 335–342 (1996)] and the 5-$HT_{1A}$ agonist flesinoxan [Grof, P., *International clinical Psychopharmacology*, 8(3), 167–72 (1993)] have shown efficacy in clinical trials for the treatment of depression. Furthermore, such agents would also stimulate the somatodendritic autoreceptors, thus hastening their desensitization and decreasing the SSRI latency period. An agent with a dual mechanism of antidepressant action would be expected to have greater efficacy and thus reduce the number of patients refractory to treatment. Indeed, buspirone augmentation has been shown to produce marked clinical improvement in patients initally unresponsive to standard antidepressant therapy [Dimitriou, E., *J. Clinical Psychopharmacol.*, 18(6), 465–469 (1998)].

Thus, it is highly desirable to provide improved compounds which both inhibit serotonin reuptake and which are agonists or partial agonists of the 5-$HT_{1A}$ receptor.

DESCRIPTION OF THE INVENTION

In accordance with this invention, there is provided a group of novel antidepressant agents of the formula:

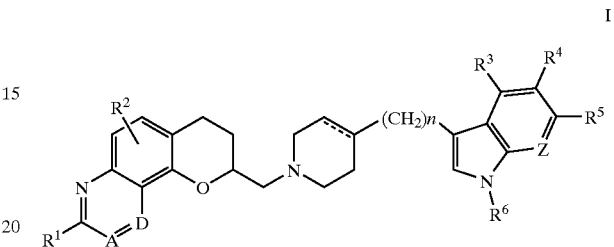

wherein $R^1$, $R^2$, $R^3$, $R^4$, $R^5$, $R^8$ and $R^9$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^6$ and $R^7$ are independently, hydrogen or alkyl of 1 to 6 carbon atoms;

A dotted line represents an optional double bond;

A and D, taken together are —$CR^9$=CH—, —N=CH—, or —$CR^7$=N—;

Z is $CR^8$ or N and n is an integer 0, 1 or 2;

or a pharmaceutically acceptable salt thereof.

In some aspects of the invention it is preferred that $R^1$ is hydrogen, hydroxy, halo, trifluoromethyl, alkyl of one to six carbon atoms, alkoxy of one to six carbon atoms, amino, mono- or di-alkylamino in which each alkyl group has one to six carbon atoms.

In other embodiments of the invention it is preferred that $R^2$ is hydrogen, hydroxy, halo, cyano, trifluoromethyl, alkyl of one to six carbon atoms or alkoxy of one to six carbon atoms.

In still other embodiments of the invention, $R^3$, $R^4$ and $R^5$ are, preferably independently selected from hydrogen, hydroxy, halo, cyano, carboxamido, alkyl of one to six carbon atoms, or alkoxy of one to six carbon atoms. $R^3$, $R^4$ and $R^5$ are still more preferably hydrogen, halogen or cyano.

In other preferred embodiments $R^1$, $R^2$, $R^3$, $R^4$ and $R^5$ are, independently selected from hydrogen.

In still other preferred embodiments of the invention A=D is —$CR^9$=CH—, and $R^9$ is hydrogen.

Z is preferably $CR^8$. When Z is $CR^8$, $R^8$ is preferably hydrogen, hydroxy, halo, cyano, carboxamido, alkyl of one to six carbon atoms, or alkoxy of one to six carbon atoms, and more preferably hydrogen, halogen or cyano Of the compounds of Formula I, the preferred members are those in which $R^1$ is hydrogen, hydroxy, halo, trifluoromethyl, alkyl of one to six carbon atoms, alkoxy of one to six carbon atoms, amino, mono- or di-alkylamino in which each alkyl group has one to six carbon atoms; $R^2$ is hydrogen, hydroxy, halo, cyano, trifluoromethyl, alkyl of one to six carbon atoms or alkoxy of one to six carbon atoms; Z is CR$^8$; R$^3$, R$^4$, R$^5$ and R$^8$ are, independently selected from hydrogen, hydroxy, halo, cyano, carboxamido, alkyl of one to six carbon atoms, or alkoxy of one to six carbon atoms; n is an integer 0 or 1; A=D is CR$^9$=CH; R$^9$ is hydrogen; and R$^6$ and the dotted line are defined as above.

Most preferred are those examples in which R$^1$ is defined as in the paragraph above, R$^2$ and R$^6$ are hydrogen, R$^3$, R$^4$, R$^5$ and R$^8$ are, independently selected from hydrogen, halo or cyano, n is 0 and the dotted line represents a double bond.

This invention relates to both the R and S stereoisomers of the aminomethyl-7,8-dihydro-6H-5-oxa-1-aza-phenanthrene, as well as to mixtures of the R and S stereoisomers. Throughout this application, the name of the product of this invention, where the absolute configuration of the aminomethyl-7,8-dihydro-6H-5-oxa-1-aza-phenanthrene is not indicated, is intended to embrace the individual R and S enantiomers as well as mixtures of the two. In some preferred embodiments of the present invention the R stereoisomer is preferred.

Where a stereoisomer is preferred, it may in some embodiments be provided substantially free of the corresponding enantiomer. Thus, an enantiomer substantially free of the corresponding enantiomer refers to a compound which is isolated or separated via separation techniques or prepared free of the corresponding enantiomer. Substantially free as used herein means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

It is further recognized that tautomers of the claimed compounds may exist, for instance, when R$^1$ is hydroxy, a tautomeric form may exist. The present invention thus encompasses tautomeric forms of compounds of the present invention.

Alkyl as used herein refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

Alkanamido as used herein refers to the group R—C(=O)—NH— where R is an alkyl group of 1 to 5 carbon atoms.

Alkanoyloxy as used herein refers to the group R—C(=O)—O— where R is an alkyl group of 1 to 5 carbon atoms.

Alkanesulfonamido as used herein refers to the group R—S(O)$_2$—NH— where R is an alkyl group of 1 to 6 carbon atoms.

Alkoxy as used herein refers to the group R—O— where R is an alkyl group of 1 to 6 carbon atoms.

Carboxamido as used herein refers to the group —CO—NH$_2$.

Carboalkoxy as used herein refers to the group R—O—C(=O)— where R is an alkyl group of 1 to 5 carbon atoms.

Halogen (or halo) as used herein refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific compounds of the present invention are:

6-[4-(5-fluoro-1H-indol-3-yl)-3,6-dihydro-2H-pyridin-1-ylmethyl]-7,8-dihydro-6H-5-oxa-1aza-phenanthrene;

(6S)-6-[4-(5-fluoro-1H-indol-3-yl)-3,6-dihydro-2H-pyridin-1-ylmethyl]-7,8-dihydro-6H-5-oxa-1aza-phenanthrene; and (6R)-6-[4-(5-fluoro-1H-indol-3-yl)-3,6-dihydro-2H-pyridin-1-ylmethyl]-7,8-dihydro-6H-5-oxa-1aza-phenanthrene; and pharmaceutical salts thereof.

Further in accordance with the present invention is provided novel intermediates of the formula:

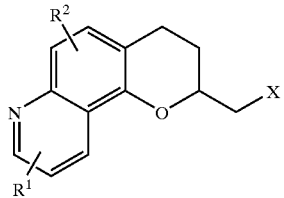

II wherein

R$^1$ and R$^2$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

X is halogen, hydroxy, alkylsulfonate of 1 to 6 carbon atoms, trifluoromethanesulfonate or benzenesulfonate, in which the benzene ring is optionally substituted with halogen, hydroxy, nitro, trifluoromethyl, cyano, alkyl of 1 to 6 carbon atoms or alkoxy of 1 to 6 carbon atoms.

Compounds of Formula II are particularly useful for the production of agents of Formula I.

Specific compounds of Formula II include:

Toluene-4-sulfonic acid 7,8-dihydro-6H-5-oxa-1-aza-phenanthren-6-ylmethyl ester;

(6S)-Toluene-4-sulfonic acid 7,8-dihydro-6H-5-oxa-1-aza-phenanthren-6-yl-methyl ester; and (6R)-Toluene-4-sulfonic acid 7,8-dihydro-6H-5-oxa-1-aza-phenanthren-6-yl-methyl ester.

Unless otherwise noted, the variables used in the following schemes are as defined above.

The 6-azaheterocyclylmethyl-7,8-dihydro-6H-5-oxa-1-aza-phenanthrenes in which R$^1$ is H are prepared as illustrated below in Scheme I. Specifically, the appropriately substituted 4-acetamido-2-hydroxyacetophenone (1) is alkylated with allyl bromide in the presence of a suitable base such as sodium

Scheme I

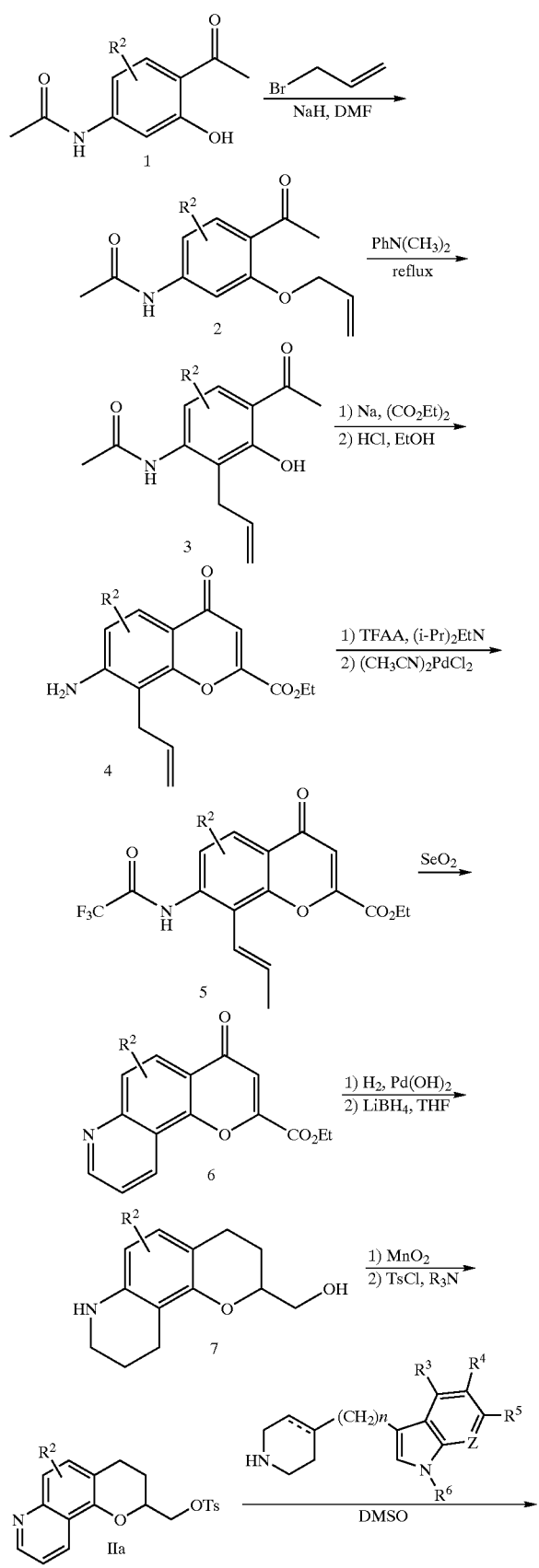

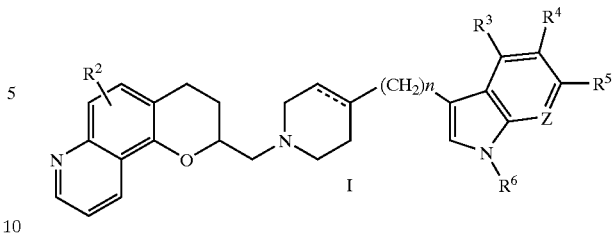

hydride to produce (2) and then heated in a high boiling solvent such as dimethylaniline to effect a Claisen rearrangement. The resulting 4-acetamido-3-allyl-2-hydroxyacetophenone (3) is then converted to the chromone under standard conditions involving condensation with diethyl oxalate and sodium in ethanol, followed by cyclization via refluxing in ethanol in the presence of an acid such as hydrochloric acid. The resulting 8-allyl-7-amino-4-oxo-4H-chromene-2-carboxylic acid ethyl ester (4) is re-protected as the trifluoroacetamide by treatment with trifluoroacetic anhydride and a tertiary base such as diisopropylethylamine. The allyl group is then isomerized by treatment with catalytic bis-acetonitrile palladium (II) chloride in refluxing methylene chloride or benzene to form (5). Allylic oxidation via treatment with an excess of selenium dioxide in refluxing dioxan is accompanied by cyclization and deprotection to afford the 5-oxa-1-aza-phenanthrene ring system (6), which characterizes the compounds of the invention. Sequential reduction of the chromone, via treatment with hydrogen in the presence of a catalyst such as 20% palladium hydroxide on carbon, and the carboethoxy group, via lithium borohydride in tetrahydrofuran, is accompanied by reduction of the quinoline (7) and necessitates re-aromatization via treatment with an oxidant such as manganese dioxide. The resulting primary alcohol is converted to the tosylate (IIa) by reaction with p-toluenesulfonyl chloride in the presence of a tertiary amine or alternatively to a halide by reaction with carbon tetrabromide or carbon tetrachloride in combination with triphenylphosphine. Replacement of the tosylate or halide with the appropriately substituted azaheterocycle in some high boiling solvent such as dimethyl sulfoxide gives the title compounds of the invention.

Compounds of the invention in which $R^1$ is alkyl may be prepared from the 8-propenyl-7-trifluoroacetamido-4-oxo-4H-chromene-2-carboxylic acid ethyl ester described above in accordance with Scheme II. The rearranged olefin (5) is treated with osmium tetroxide and sodium periodate to give the o-trifluoro-acetamidobenzaldehyde (8). Condensation with the appropriate triphenyl-phosphorylidene ketone under Wittig conditions gives the o-trifluoroacetamidostyryl ketone (9), which upon treatment with acid cyclizes to give the 5-oxa-1-aza-phenanthrene ring system of the title compounds (10). Reduction, re-aromatization and tosylation as above gives the 7,8-dihydro-6H-5-oxa-1-aza-phenanthren-6-methyltosylate. Replacement of the tosylate with the appropriately substituted azaheterocycle as above gives the title compounds of the invention. Substitution of trimethyl phosphonoacetate for the triphenylphosphorylidene ketone in the Wittig procedure above, followed by cyclization in acid gives the compounds of the invention in which $R^1$ is hydroxy. Alkylation of this hydroxy derivative by a suitable alkyl halide or tosylate in the presence of base gives the compounds of the invention in which $R^1$ is alkoxy. Treatment of the hydroxy derivative with an inorganic acid chloride such as phosphoryl chloride or bromide gives the compounds of the invention in which $R^1$ is halo. Substitution of diethyl cyanomethylphosphonate for the triphenylphosphorylidene ketone in the Wittig procedure above, followed by cyclization in acid gives the compounds of the invention in which $R^1$ is amino.

Scheme II

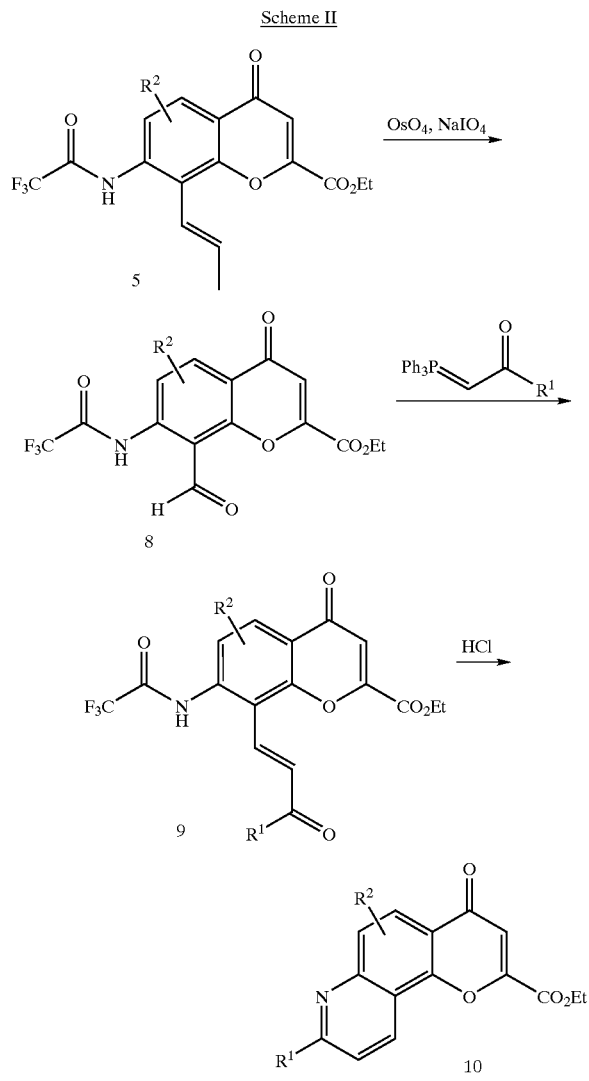

Compounds of the invention in which $R^2$ is attached to position 10 of the 7,8-dihydro-6H-5-oxa-1-aza-phenanthrene may be alternatively prepared by a variation of the Skraup quinoline synthesis according to the Scheme III below. The appropriately substituted chroman methyltosylate (11) is nitrated under standard conditions with nitric acid in a solvent such as dichloroethane and the resulting nitro Scheme III

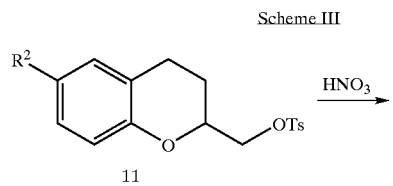

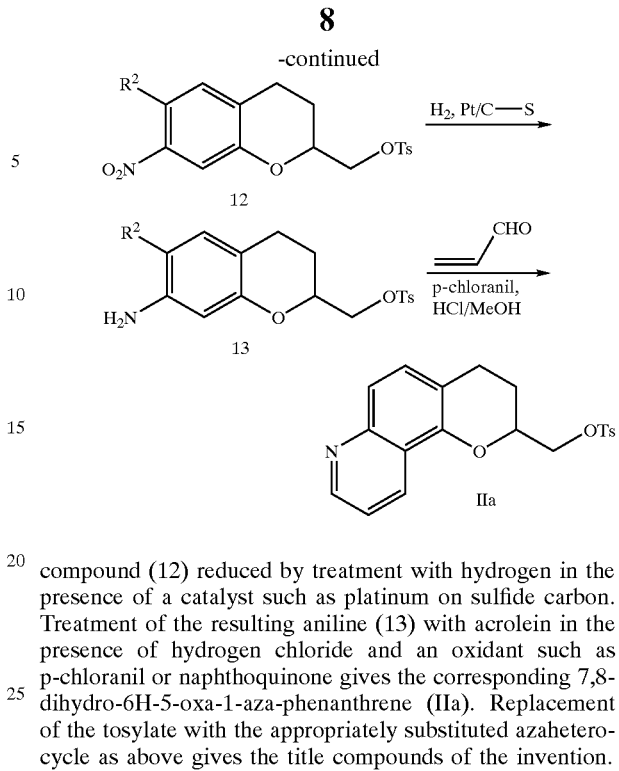

compound (12) reduced by treatment with hydrogen in the presence of a catalyst such as platinum on sulfide carbon. Treatment of the resulting aniline (13) with acrolein in the presence of hydrogen chloride and an oxidant such as p-chloranil or naphthoquinone gives the corresponding 7,8-dihydro-6H-5-oxa-1-aza-phenanthrene (IIa). Replacement of the tosylate with the appropriately substituted azaheterocycle as above gives the title compounds of the invention.

The compounds of the invention in which $R^1$ and $R^2$ are hydrogen may be alternatively prepared as shown in Scheme IV below. The appropriately protected (TBS represents t-butyldimethylsilyl, Boc is t-butoxycarbonyl) 7-amino-8-methyl-chroman-2-methanol (14) is metallated with sec-butyl lithium and alkylated with allyl bromide. The olefin (15) is then treated with osmium tetroxide and sodium periodate as described above to give the aldehyde, which spontaneously cyclizes to give the protected cyclic aminal. Following deprotection of the primary alcohol with tetra-n-butylammonium fluoride (TBAF) to provide (16), dehydration and aromatization is effected by a period of heating in o-dichlorobenzene. The resulting (7,8-dihydro-6H-5-oxa-1-aza-phenanthren-6-yl)-methanol (IIb) is converted to the compounds of the invention as described above.

Scheme IV

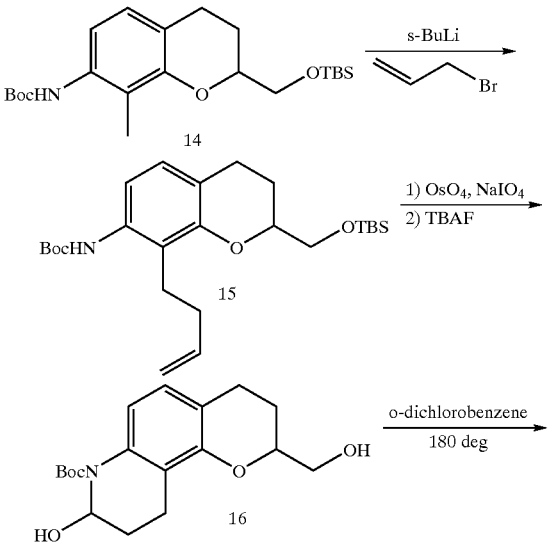

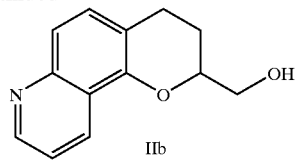
IIb

The acetophenones, chromans and azaheterocycles appropriate to the above chemistry are known compounds or they can be prepared by one schooled in the art. The compounds of the invention may be resolved into their enantiomers by conventional methods involving partial crystallization of a diastereomeric salt, separation on a chiral HPLC column or enzymatic resolution of a suitable intermediate or, in the case of the compounds of the invention in which $R^1$ and $R^2$ are hydrogen, the individual enantiomers may be prepared directly by substitution of the known [Tetrahedron 54(25) 7081, (1998)] (R)- or (S)-[2-(t-butyl-dimethyl-silanyloxymethyl)-8-methyl-chroman-7-yl]-carbamic acid t-butyl ester for the racemic starting material in the procedure above.

Like the antidepressants fluoxetine, paroxetine and sertraline, the compounds of this invention have the ability to potently block the reuptake of the brain neurotransmitter serotonin. They are thus useful for the treatment of depression and other diseases commonly treated by the administration of serotonin selective reuptake inhibitor (SSRI) antidepressants, such as obsessive compulsive disorder, panic attacks, generalized anxiety disorder, social anxiety disorder, sexual dysfunction, eating disorders, obesity, addictive disorders caused by ethanol or cocaine abuse and related illnesses. Moreover, the compounds of this invention have affinity for agonist or partial agonist activity at brain $5\text{-}HT_{1A}$ serotonin receptors. The $5\text{-}HT_{1A}$ partial agonists buspirone and gepirone have demonstrated anxiolytic and antidepressant properties in clinical trials and the $5\text{-}HT_{1A}$ full agonist flesinoxan has been shown to be an effective antidepressant. The compounds of the invention are thus exceedingly interesting and useful for treating depressive illnesses.

A protocol similar to that used by Cheetham et. al. (Neuropharmacol. 32:737, 1993) was used to determine the affinity of the compounds of the invention for the serotonin transporter. The compound's ability to displace $^3$H-paroxetine from male rat frontal cortical membranes was determined using a Tom Tech filtration device to separate bound from free $^3$H-paroxetine and a Wallac 1205 Beta Plate® counter to quantitate bound radioactivity. $K_j$'s thus determined for standard clinical antidepressants are 1.96 nM for fluoxetine, 14.2 nM for imipramine and 67.6 nM for zimelidine. A strong correlation has been found between $^3$H-paroxetine binding in rat frontal cortex and $^3$H-serotonin uptake inhibition.

High affinity for the serotonin $5\text{-}HT_{1A}$ receptor was established by testing the claimed compound's ability to displace [$^3$H] 8-OHDPAT (dipropylaminotetralin) from the $5\text{-}HT_{1A}$ serotonin receptor following a modification of the procedure of Hall et al., J. Neurochem. 44, 1685 (1985) which utilizes CHO cells stably transfected with human $5\text{-}HT_{1A}$ receptors. The $5\text{-}HT_{1A}$ affinities for the compounds of the invention are reported below as $K_j$'s.

Agonist activity at $5\text{-}HT_{1A}$ receptors was established by using a $^{35}$S-GTPγS binding assay similar to that used by Lazareno and Birdsall (Br. J. Pharmacol. 109: 1120, 1993), in which the test compound's ability to affect the binding of $^{35}$S-GTPγS to membranes containing cloned human $5\text{-}HT_{1A}$ receptors was determined. Agonists produce an increase in binding whereas antagonists produce no increase but rather reverse the effects of the standard agonist 8-OHDPAT. The test compound's maximum stimulatory effect is represented as the $E_{max}$, while its potency is defined by the $EC_{50}$.

The results of the three standard experimental test procedures described in the preceding three paragraphs were as follows:

| Compound | 5-HT Transporter Affinity KI (nM) | $5\text{-}HT_{1A}$ Receptor Affinity KI (nM) | $5\text{-}HT_{1A}$ Function $EC_{50}$ (nM) ($E_{max}$) |
|---|---|---|---|
| Example 1 | 8.00 | 60.92 | 103.0 (49.0) |
| Example 2 | 5.96 | 88.60 | (5.00) |
| Example 3 | 6.00 | 82.32 | 78.9 (52.0) |

Hence, the compounds of this invention are combined serotonin reuptake inhibitors/$5\text{-}HT_{1A}$ agonists and are useful for the treatment of depression and other conditions related to or affected by the reuptake of serotonin and by the serotonin 1A receptor, such as depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorder (including trichotillomania), social anxiety disorder, generalized anxiety disorder, obesity, eating disorders such as anorexia nervosa, bulimia nervosa, vasomotor flushing, cocaine and alcohol addition, sexual dysfunction (including premature ejaculation), and related illnesses.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remingtons Pharmaceutical Sciences,* 17th edition, ed. Alfonoso R. Gennaro, Mack Publishing Company, Easton, Pa. (1985). Pharmaceutical acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide as used herein means either directly administering a compound or composition of the present invention, or administering a prodrug, derivative or analog which will form an equivalent amount of the active compound or substance within the body.

The present invention includes prodrugs of compounds of Formula I. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Deliver Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

INTERMEDIATE 1

8-Allyl-4-oxo-7-(2,2,2-trifluoro-acetylamino)-4H-chromene-2-carboxylic acid ethyl ester To 8-allyl-7-amino-4-oxo-4H-chromene-2-carboxylic acid ethyl ester (8.6 g, 32 mmole) in 400 mL of methylene chloride was added first N,N-diisopropyl-ethylamine (6.5 g, 50 mmole) and then, while cooling the mixture in an ice bath, trifluoroacetic anhydride (10.5 g, 50 mmole). The mixture was stirred at room temperature for one hour, then washed with 200 mL portions of 2 N aqueous HCl, saturated aqueous sodium bicarbonate, and saturated brine, dried over sodium sulfate, filtered and concentrated in vacuum to give 12.2 g of the title compound as a pale yellow solid, m.p. 136–137° C.

Elemental Analysis for: $C_{17}H_{14}F_3NO_5$ Calc'd: C, 55.29; H, 3.82; N, 3.79 Found: C, 55.28; H, 3.79; N, 3.76

INTERMEDIATE 2

4-Oxo-8-propenyl-7-(2,2,2-trifluoro-acetylamino)-4H-chromene-2-carboxylic acid ethyl ester To 8-allyl-4-oxo-7-(2,2,2-trifluoro-acetylamino)-4H-chromene-2-carboxylic acid ethyl ester (12.2 g, 32 mmole) in 500 mL of methylene chloride was added 1.5 g (5.8 mmole) of bis(acetonitrile) palladium (II) chloride. The mixture was refluxed under nitrogen for 24 hours. Upon cooling to room temperature, the mixture was filtered through 75 g of silica gel, with additional methylene chloride as needed to fully elute the product. Concentration in vacuum gave 10.4 g of the title compound as a yellow solid, m.p. 140–141° C.

Elemental Analysis for: $C_{17}H_{14}F_3NO_5$ Calc'd: C, 55.29; H, 3.82; N, 3.79 Found: C, 55.24; H, 3.89; N, 3.75

INTERMEDIATE 3

8-Oxo-8H-5-oxa-1-aza-phenanthrene-6-carboxylic acid ethyl ester

To 4-oxo-8-propenyl-7-(2,2,2-trifluoro-acetylamino)-4H-chromene-2-carboxylic acid ethyl ester (3.7 g, 10 mmole) in 100 mL of dioxan was added 4.4 g (40 mmole) of selenium dioxide. The mixture was refluxed under nitrogen for 5 hours. An additional 1.0 g of selenium dioxide was added and reflux continued for 8 hours. After the reaction had cooled, 500 mL of water was added and the mixture was extracted with first 300 mL and then 200 mL of ethyl acetate. The combined organic extracts were washed with water and with saturated brine, dried over sodium sulfate, filtered and evaporated in vacuum to give 2.0 g of the title compound as a yellow solid. An analytically pure sample of yellow solid (m.p. 146–147° C.) was obtained by column chromatography on silica gel with 0–5% ethyl acetate/methylene chloride as eluant.

Elemental Analysis for: $C_{15}H_{11}NO_4 \cdot 1.1H_2O$ Calc'd: C, 62.33; H, 4.60; N, 4.85 Found: C, 62.09; H, 4.15; N, 4.79

INTERMEDIATE 4

(1,3,4,6,7,8-Hexahydro-2H-5-oxa-1-aza-phenanthren-6-yl)-methanol

8-Oxo-8H-5-oxa-1-aza-phenanthrene-6-carboxylic acid ethyl ester (2.0 g, 7.4 mmole) was dissolved in 200 mL of ethanol and 0.50 g of 20% palladium hydroxide on carbon added. The mixture was treated with 60 psi of hydrogen on a Parr apparatus for 48 hours, then filtered through celite and concentrated in vacuum. Thin layer chromatography on silica gel vs. a starting material standard indicated that the reaction was incomplete. The material was redissolved in 150 mL of acetic acid, 0.50 g of 20% palladium hydroxide on carbon added, and the mixture again treated with 60 psi of hydrogen for 48 hours. It was then filtered through celite, concentrated in vacuum and column chromatographed on silica gel with 2% ethanol in chloroform as eluant to give 0.80 g of 1,3,4,6,7,8-hexahydro-2H-5-oxa-1-aza-phenanthrene-6-carboxylic acid ethyl ester. $^1$H-NMR (CDCl$_3$): doublet 6.65 δ (1 H); doublet 6.1 δ (1 H); multiplet 4.7 δ (1 H); quartet 4.25 δ (2 H); broad singlet 3.65 δ (1 H); multiplet 3.2 δ (2 H); multiplet 2.65 δ (4 H); multiplet 2.2 δ (2 H); multiplet 1.95 δ(2 H); triplet 1.25 δ (3 H).

To 1,3,4,6,7,8-hexahydro-2H-5-oxa-1-aza-phenanthrene-6-carboxylic acid ethyl ester (0.80 g, 3.1 mmole) in 25 mL of tetrahydrofuran was added 0.22 g (10 mmole) of lithium borohydride. The mixture was stirred for 48 hours at room temperature. Methanol (5 mL) was added and stirring at room temperature continued for an additional hour. The mixture was then diluted to 300 mL with ethyl acetate and washed with 100 mL portions of water and saturated brine and dried over sodium sulfate. Filtration and concentration in vacuum gave 0.83 g of the title compound as a white solid. $^1$H-NMR (CDCl$_3$): doublet 6.65 δ (1 H); doublet 6.1 δ (1 H); multiplet 4.1 δ (1 H); multiplet 3.8 δ (2 H); multiplet 3.2 δ (2 H); broad singlet 2.8 δ (1 H); multiplet 2.55 δ (4 H); multiplet 1.9 δ (2 H); multiplet 1.2 δ (2 H).

INTERMEDIATE 5

(7,8-Dihydro-6H-5-oxa-1-aza-phenanthren-6-yl)-methanol

To (1,3,4,6,7,8-hexahydro-2H-5-oxa-1-aza-phenanthren-6-yl)-methanol (0.90 g, 4.0 mmole) in 150 mL of toluene was added 1.8 g (20 mmole) of manganese dioxide. The mixture was refluxed under nitrogen for 24 hours. It was then filtered through celite, concentrated in vacuum and column chromatographed on silica gel with 0–2% methanol/chloroform as eluant. Concentration of the product fractions in vacuum gave 0.30 g of the title compound as an orange oil. $^1$H-NMR (CDCl$_3$): doublet 8.8 δ (1 H); doublet 8.4 δ (1 H); doublet 7.6 δ (1 H); doublet 7.35 δ (1 H); doublet of doublets 7.25 δ (1 H); multiplet 4.25 δ (1 H); multiplet 3.95 δ (2 H); multiplet 2.9 δ (2 H); multiplet 2.05 δ (2 H).

INTERMEDIATE 6

Toluene-4-sulfonic acid 7,8-dihydro-6H-5-oxa-1-aza-phenanthren-6-ylmethyl ester (7,8-Dihydro-6H-5-oxa-1-aza-phenanthren-6-yl)-methanol (0.27 g, 1.3 mmole) was dissolved in 75 mL of methylene chloride and p-toluenesulfonyl chloride (0.60 g, 3.1 mmole) added. The mixture was placed in an ice/isopropanol bath and first N,N-diisopropylethylamine (0.55 mL, 3.1 mmole) and then N,N-dimethyaminopyridine added. The mixture was allowed to stir under nitrogen for 5 days. It was washed with 150 mL portions of 2 N aqueous HCl, saturated aqueous sodium bicarbonate and saturated brine, dried over magnesium sulfate, filtered and concentrated in vacuum to an orange oil. Column chromatography on silica gel with 0–5% methanol/methylene chloride gave 0.22 g of the title compound. $^1$H-NMR (CDCl$_3$): doublet 8.8 δ (1 H); doublet 8.25 δ (1 H); doublet 7.8 δ (2 H); doublet 7.6 δ(1 H); multiplet 7.3 δ (4 H); multiplet 4.4 δ (1 H); doublet 4.3 δ (2 H); multiplet 2.9 δ (2 H); singlet 2.4 δ (3 H); multiplet 2.0 δ (2 H).

EXAMPLE 1

6-[4-(5-Fluoro-1H-indol-3-yl)-3,6-dihydro-2H-pyridin-1-ylmethyl]-7,8-dihydro-6H-5-oxa-1aza-phenanthrene Toluene-4-sulfonic acid 7,8-dihydro-6H-5-oxa-1-aza-phenanthren-6-ylmethyl ester (0.22 g, 1.67 mmole) and 5-fluoro-3-(1,2,3,6-tetrahydro-4-pyridinyl)-1H-indole (4.0 g, 1.8 mmole) were combined in 200 mL of DMSO and heated at 75–80° C. under nitrogen for 13 hours. After cooling to room temperature, the mixture was partitioned between 400 mL each of ethyl acetate and saturated sodium bicarbonate solution. The organic phase was removed, washed with saturated brine, dried over magnesium sulfate and concentrated to an oil in vacuum. This was column chromatographed on silica gel using first methylene chloride to elute impurities and then 5% methanol in methylene chloride to elute the product, 0.19 g of a yellow oil. The oil was recrystallized from isopropanol with the addition of 0.05 g of oxalic acid to give 0.043 g of the title compound as a yellow solid (m.p. 148° C.).

Elemental Analysis for: C$_{26}$H$_{24}$FN$_3$O.C$_2$H$_2$O$_4$.H$_2$O Calc'd: C, 58.92; H, 4.92; N, 6.83 Found: C, 58.56; H, 4.45; N, 6.62

INTERMEDIATE 7

(2S)-[8-But-3-enyl-2-(tert-butyl-dimethyl-silanyloxymethyl)-chroman-7-yl]-carbamic acid tert-butyl ester To a solution of (2S)-[2-(tert-butyl-dimethyl-silanyloxymethyl)-8-methyl-chroman-7-yl]-carbamic acid tert-butyl ester (0.41 g, 1.0 mmole) in anhydrous tetrahydrofuran (20 mL) containing 0.010 g of 1,10-phenanthroline at –40° C. was slowly added 2.4 equivalents of 1.3 M s-butyl lithium. After 1 equivalent of s-butyl lithium had been added, the deep red color of the indicator became apparent. The reaction was allowed to stand for 1.5 hours after which allyl bromide (0.24 g, 2.0 mmole) was added. After an additional 4 hours the reaction was quenched with water (4 mL). The reaction mixture was diluted with ether (250 mL) and washed with saturated aqueous sodium bicarbonate (50 mL). The organic layer was separated and the solvent removed under vacuum. Column chromatography on silica gel (5% ethyl acetate/hexane) afforded 0.38 g (85%) of the title compound as an oil, [M+H]$^+$: 448, $[\alpha]^{25}_D$=+34.0° (c=1.03, THF).

Elemental Analysis for: C$_{25}$H$_{41}$NO$_4$Si.0.15CH$_2$Cl$_2$ Calc'd: C, 65.61; H, 9.04; N 3.04 Found: C, 65.61, H, 9.00, N 3.02

INTERMEDIATE 8

(6S)-2-Hydroxy-6-hydroxymethyl-3,4,7,8-tetrahydro-2H,6H-5-oxa-1-aza-phenanthrene-1-carboxylic acid tert-butyl ester To a solution of (2S)-[8-but-3-enyl-2-(tert-butyl-dimethyl-silanyloxymethyl)-chroman-7-yl]-carbamic acid tert-butyl ester (0.33 g, 0.74 mmole) in anhydrous tetrahydrofuran (15 mL) and water (3 mL) at 0° C. was added osmium tetroxide (0.1 mL, 5% in water), followed by sodium periodate (0.47 g, 2.2 mmole). The mixture was stirred for 48 hours. The solution was diluted with ethyl acetate and the organic layer was washed with water, dried over $Na_2SO_4$, filtered, and the solvent evaporated in vacuum. Column chromatography on silica gel (80% ethyl acetate/hexane) afforded 0.19 g (76%) of the title compound as an oil, the t-butyldimethylsilyl protecting group having been cleave in the course of the reaction. $[\alpha]^{25}_D$=+40.66° (c=7.7, DMSO)

Elemental analysis for: $C_{18}H_{25}NO_5$ Calc'd: C, 64.46; H, 7.51; N 4.18 Found: C, 68.18; H, 7.62; N 4.06

INTERMEDIATE 9

(6S)-(7,8-Dihydro-6H-5-oxa-1-aza-phenanthren-6-yl)-methanol

A solution of (6S)-2-hydroxy-6-hydroxymethyl-3,4,7,8-tetrahydro-2H,6H-5-oxa-1-aza-phenanthrene-1-carboxylic acid tert-butyl ester (0.33 mg, 1.0 mmole) in o-dichlorobenzene (15 mL) was stirred at 180° C. for 4 hours. The solvent was removed in vacuum. The residue was purified by column chromatography on silica gel (50% methylene chloride/hexane) to afford 0.15 g (71%) of the title compound as a solid, mp 128° C., $[\alpha]^{25}_D$=+74.19° (c=7.7, DMSO).

Elemental analysis for: $C_{13}H_{13}NO_2.0.15H_2O$ Calc'd: C, 71.64; H, 6.15; N 6.43 Found: C, 71.63; H, 6.12; N 6.33

INTERMEDIATE 10

(6S)-Toluene-4-sulfonic acid 7,8-dihydro-6H-5-oxa-1-aza-phenanthren-6-ylmethyl ester A solution of (6S)-(7,8-dihydro-6H-5-oxa-1-aza-phenanthren-6-yl)-methanol (0.14 g, 0.65 mmole) and p-toluenesulfonyl chloride (0.25 g, 1.3 mmole) in anhydrous pyridine (50 mL) was allowed to stir for 24 hours and then the solvent was removed in vacuum. The residue was dissolved in ethyl acetate (50 mL) and washed with water (3×30 mL). The organic layer was dried over sodium sulfate and filtered, and the solvent was removed under vacuum. Column chromatography on silica gel (50% methylene chloride/hexane) afforded 0.23 g (96%) of the title compound as a solid, mp 123° C., $[\alpha]^{25}_D$=+51.22° (4.92, $CHCl_3$).

Elemental analysis for: $C_{20}H_{19}NO_4S.0.1CH_2Cl_2$ Calc'd: C, 63.88; H, 5.12; N 3.71 Found: C, 63.55; H, 5.00; N 3.60

EXAMPLE 2

(6S)-6-[4-(5-Fluoro-1H-indol-3-yl)-3,6-dihydro-2H-pyridin-1-ylmethyl]-7,8-dihydro-6H-5-oxa-1aza-phenanthrene A solution of (6S)-toluene-4-sulfonic acid 7,8-dihydro-6H-5-oxa-1-aza-phenanthren-6-ylmethyl ester (0.12 g, 0.33 mmole) and 5-fluoro-3-(1,2,3,6-tetrahydro-4-pyridinyl)-1H-indole (0.14 g, 0.65 mmole) in anhydrous DMSO (25 mL) was stirred at 80° C. for 2 hours. The reaction mixture was then poured into chloroform (100 mL) and washed with water (3×40 mL). The organic layer was dried over sodium sulfate and filtered, and the solvent was removed under vacuum. Column chromatography on silica gel (5% methanol/ethyl acetate) afforded 0.083 g (62%) of the title compound. The oxalate salt was prepared in ethyl acetate and ethanol and had mp 210° C. and $[\alpha]^{25}_D$=+71.43° (c=4.68, DMSO).

Elemental analysis for: $C_{26}H_{24}FN_3O.2C_2H_2O_4$ Calc'd: C, 60.64; H, 4.75; N, 7.07 Found: C, 60.93; H, 4.80; N, 7.29

INTERMEDIATE 11

(2R)-[8-But-3-enyl-2-(tert-butyl-dimethyl-silanyloxymethyl)-chroman-7-yl]-carbamic acid tert-butyl ester To a solution of (2R)-[2-(tert-butyl-dimethyl-silanyloxymethyl)-8-methyl-chroman-7-yl]-carbamic acid tert-butyl ester (0.41 g, 1 mmole) in anhydrous tetrahydrofuran (20 mL) containing 10 mg of 1,10-phenanthroline at −40° C. was slowly added 2.4 equivalents of 1.3 M s-butyl lithium. After 1 equivalent of s-butyl lithium had been added, the deep red color of the indicator became apparent. The reaction was allowed to stand for 1.5 hours, after which allyl bromide (0.24 g, 2.0 mmole) was added. The reaction was allowed to stand for an additional 4 hours and then was quenched with water (4 mL). The reaction mixture was next diluted with ether (250 mL) and washed with saturated aqueous sodium bicarbonate (50 mL). The organic layer was separated and the solvent removed under vacuum. Column chromatography on silica gel (5% methylene chloride/hexane) afforded 0.37 g (75%) of the title compound as an oil, $[\alpha]^{25}_D$=−32.42° (3.7, THF).

Elemental analysis for: $C_{25}H_{41}NO_4Si.0.05CH_2Cl_2$ Calc'd: C, 66.57; H, 9.16; N 3.09 Found: C, 66.46; H, 9.31; N 2.97.

INTERMEDIATE 12

(6R)-6-(tert-Butyl-dimethyl-silanyloxymethyl)-2-hydroxy-3,4,7,8-tetrahydro-2H,6H-5-oxa-1-aza-phenanthrene-1-carboxylic acid tert-butyl ester To a solution of (2R)-[8-but-3-enyl-2-(tert-butyl-dimethyl-silanyloxymethyl)-chroman-7-yl]-carbamic acid tert-butyl ester (3.6 g, 8.0 mmole) in tetrahydrofuran (150 mL) and water (15 mL) at 0° C. was added osmium tetroxide (0.4 mL, 5% in water), followed by sodium periodate (5.16 g, 24 mmole). The mixture was stirred for 6 hours. The solution was diluted with ethyl acetate and the organic layer was washed with water, dried over sodium sulfate, filtered, and the solvent evaporated in vacuum. Column chromatography on silica gel (10% ethyl acetate/hexane) afforded 2.92 g (81%) of the title compound as an oil, $[\alpha]^{25}_D$=−36.75° (4.9, THF).

Elemental analysis for: $C_{24}H_{39}NO_5Si$ Calc'd: C, 64.11; H, 8.79; N, 3.11 Found: C, 63.64; H, 8.09; N, 2.90

INTERMEDIATE 13

(6R)-6-(tert-Butyl-dimethyl-silanyloxymethyl)-7,8-dihydro-6H-5-oxa-1-aza-phenanthrene A solution of (6R)-6-(tert-butyl-dimethyl-silanyloxymethyl)-2-hydroxy-3,4,7,8-tetrahydro-2H,6H-5-oxa-1-aza-phenanthrene-1-carboxylic acid tert-butyl ester (0.45 g, 1.0 mmole) in o-dichlorobenzene (150 mL) was stirred at 180° C. for 4 hours. The solvent was removed in vacuum. The residue was purified by column chromatography on silica gel (10% methylene chloride/hexane) to afford 0.23 g (70%) of the title compound as an oil, $[\alpha]^{25}_D$=−61.94° (c=10.7, THF).

Elemental analysis for: $C_{19}H_{27}NO_2Si.0.1CH_2Cl_2$ Calc'd: C, 67.87; H, 8.11; N, 4.14 Found: C, 67.69; H, 7.89; N, 4.05

INTERMEDIATE 14

(6R)-(7,8-Dihydro-6H-5-oxa-1-aza-phenanthren-6-yl)-methanol

To a solution of (6R)-6-(tert-butyl-dimethyl-silanyloxymethyl)-7,8-dihydro-6H-5-oxa-1-azaphenanthrene (0.60 g, 1.82 mmole) in tetrahydrofuran (50 mL) was added tetra-n-butylammonium fluoride (2 mL, 1M in THF). The reaction mixture was stirred for 20 minutes, then diluted with ethyl acetate and washed with water, dried over sodium sulfate, and the solvent removed in vacuum. The residue was purified by column chromatography on silica gel (50% methylene chloride/hexane) to afford 0.38 g (98%) of the title compound as a white solid, mp 128° C., $[\alpha]^{25}{}_D$=+113.81° (c=5.9, CHCl$_3$).

Elemental analysis for: $C_{13}H_{13}NO_2 \cdot 0.2C_6H_{14}$+ $0.1CH_2Cl_2$ Calc'd: C, 71.64; H, 6.15; N, 6.43 Found: C, 71.63; H, 6.12; N, 6.33

INTERMEDIATE 15

(6R)-Toluene-4-sulfonic acid 7,8-dihydro-6H-5-oxa-1-aza-phenanthren-6-ylmethyl ester A solution of (6R)-(7,8-dihydro-6H-5-oxa-1-aza-phenanthren-6-yl)-methanol (0.38 g, 1.8 mmole) and p-toluenesulfonyl chloride (0.67 g, 3.5 mmole) in anhydrous pyridine (50 mL) was allowed to stir for 24 hours and then the solvent was removed in vacuum. The residue was dissolved in ethyl acetate (50 mL) and washed with water (3×30 mL). The organic layer was dried over sodium sulfate and filtered, and the solvent was removed under vacuum. Column chromatography on silica gel (50% methylene chloride/hexane) afforded 0.62 g (95%) of the title compound as a solid, mp 123° C., $[\alpha]^{25}{}_D$=-27.71° (c=5.0, CHCl$_3$).

Elemental analysis for: $C_{20}H_{19}NO_4S \cdot 0.05CH_2Cl_2$ Calc'd: C, 64.44; H, 5.15; N, 3.74 Found: C, 64.13; H, 5.00; N, 3.76

EXAMPLE 3

(6R)-6-[4-(5-Fluoro-1H-indol-3-yl)-3,6-dihydro-2H-pyridin-1-ylmethyl]-7,8-dihydro-6H-5-oxa-1aza-phenanthrene A solution of (6R)-toluene-4-sulfonic acid 7,8-dihydro-6H-5-oxa-1-aza-phenanthren-6-ylmethyl ester (0.17 g, 0.47 mmole) and 5-fluoro-3-(1,2,3,6-tetrahydro-4-pyridinyl)-1H-indole (0.20 g, 0.94 mmole) in anhydrous DMSO (25 mL) was stirred at 80° C. for 2 hours. The reaction mixture was then poured into chloroform (100 mL) and washed with water (3×40 mL). The organic layer was dried over sodium sulfate and filtered, and the solvent was removed under vacuum. Column chromatography on silica gel (5% methanol/ethyl acetate) afforded 0.11 g (55%) of the title compound. The fumarate salt was prepared in ethyl acetate and isopropyl alcohol and had mp 210° C. and $[\alpha]^{25}{}_D$=-60.03° (c=4.5, DMSO).

Elemental analysis for: $C_{26}H_{24}FN_3O \cdot C_4H_4O_4 \cdot H_2O$ Calc'd: C, 65.61; H, 5.77; N, 7.42 Found: C, 65.28; H, 5.43; N, 7.03

What is claimed is:

1. A compound of formula I

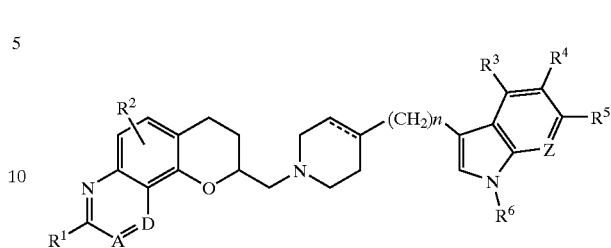

wherein $R^1$, $R^2$, $R^3$, $R^4$, $R^5$, $R^8$ and $R^9$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^6$ is hydrogen or alkyl of 1 to 6 carbon atoms;

A dotted line represents an optional double bond;

A and D, taken together are —$CR^9$=CH—;

Z is $CR^8$ or N and n is an integer 0, 1 or 2;

or a pharmaceutically acceptable salt thereof.

2. A compound of claim 1 wherein $R^1$ is hydrogen, hydroxy, halo, trifluoromethyl, alkyl of one to six carbon atoms, alkoxy of one to six carbon atoms, amino, mono- or di-alkylamino in which each alkyl group has one to six carbon atoms.

3. A compound of claim 1 wherein $R^2$ is hydrogen, hydroxy, halo, cyano, trifluoromethyl, alkyl of one to six carbon atoms or alkoxy of one to six carbon atoms.

4. A compound of claim 1 wherein $R^3$, $R^4$ and $R^5$ are, independently selected from hydrogen, hydroxy, halo, cyano, carboxamido, alkyl of one to six carbon atoms, and alkoxy of one to six carbon atoms.

5. A compound of claim 1 wherein $R^1$, $R^2$, $R^3$, $R^4$ and $R^5$ are, independently selected from hydrogen, halogen and cyano.

6. A compound of claim 1 wherein A=D is —CH=CH—.

7. A compound of claim 1 wherein Z is $CR^8$.

8. A compound of claim 7 wherein $R^8$ is hydrogen, hydroxy, halo, cyano, carboxamido, alkyl of one to six carbon atoms, or alkoxy of one to six carbon atoms.

9. A compound of claim 1 in which $R^1$ is hydrogen, hydroxy, halo, trifluoromethyl, alkyl of one to six carbon atoms, alkoxy of one to six carbon atoms, amino, mono- or di-alkylamino in which each alkyl group has one to six carbon atoms; $R^2$ is hydrogen, hydroxy, halo, cyano, trifluoromethyl, alkyl of one to six carbon atoms or alkoxy of one to six carbon atoms; $R^3$, $R^4$ and $R^5$ are independently selected from hydrogen, hydroxy, halo, cyano, carboxamido, alkyl of one to six carbon atoms, and alkoxy of one to six carbon atoms; n is an integer 0 or 1; and A=D is $CR^9$=CH and $R^9$ is H; or a pharmaceutically acceptable salt thereof.

10. A compound of claim 2 in which $R^2$ and $R^6$ are hydrogen, and $R^3$, $R^4$ and $R^5$ are independently selected from hydrogen, halo and cyano, n is 0 and the dotted line represents a double bond; or a pharmaceutically acceptable salt thereof.

11. A compound of claim 1 which is the R stereoisomer substantially free of the S stereoisomer.

12. The compound of claim 1 which is 6-[4-(5-fluoro-1H-indol-3-yl)-3,6-dihydro-2H-pyridin-1-ylmethyl]-7,8-dihydro-6H-5 -oxa-1aza-phenanthrene or a pharmaceutically acceptable salt thereof.

13. The compound of claim 1 which is (6S)-6-[4-(5-fluoro-1H-indol-3-yl)-3,6-dihydro-2H-pyridin-1-ylmethyl]-7,8-dihydro-6H-5-oxa-1aza-phenanthrene or a pharmaceutically acceptable salt thereof.

14. The compound of claim 1 which is (6R)-6-[4-(5-fluoro-1H-indol-3-yl)-3,6-dihydro-2H-pyridin-1-ylmethyl]-7,8-dihydro-6H-5-oxa-1aza-phenanthrene or a pharmaceutically acceptable salt thereof.

15. A pharmaceutical composition comprising a therapeutically effective amount of a compound of Formula I

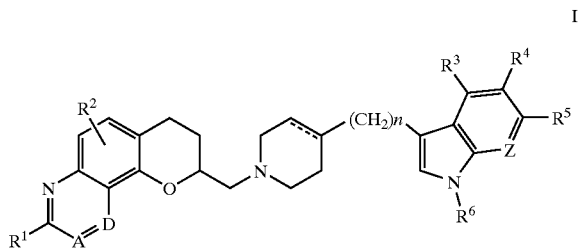

I wherein $R^1$, $R^2$, $R^3$, $R^4$, $R^5$, $R^8$ and $R^9$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^6$ is hydrogen or alkyl of 1 to 6 carbon atoms;

A dotted line represents an optional double bond;

A and D, taken together are —$CR^9$=CH—,

Z is $CR^8$ or N and n is an integer 0, 1 or 2;

or a pharmaceutically acceptable salt thereof, and a pharmaceutically acceptable carrier or excipient.

16. A method of treating a subject suffering from a condition selected from the group consisting of depression, anxiety, panic disorder, post-traumatic stress disorder, premenstrual dysphoric disorder, obsessive compulsive disorder, social anxiety disorder, generalized anxiety disorder, obesity, anorexia nervosa, bulimia nervosa, and premature ejaculation which comprises providing to the subject suffering from said condition, a therapeutically effective amount of a compound of formula I

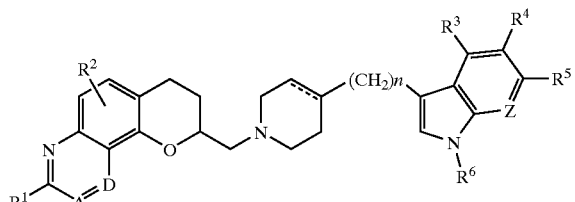

wherein $R^1$, $R^2$, $R^3$, $R^4$, $R^5$, $R^8$ and $R^9$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^6$ is hydrogen or alkyl of 1 to 6 carbon atoms;

A dotted line represents an optional double bond;

A and D, taken together are —$CR^9$=CH—;

Z is $CR^8$ or N and n is an integer 0, 1 or 2;

or a pharmaceutically acceptable salt thereof.

17. The method of claim 16 wherein the condition is depression.

18. The method of claim 16 wherein the condition is obsessive compulsive disorder, panic attacks, generalized anxiety disorder or social anxiety disorder.

19. The method of claim 16 wherein the condition is anxiety or post-traumatic stress disorder.

20. The method of claim 16 wherein the condition is premenstrual dysphoric disorder.

21. The method of claim 16 wherein the condition is obesity.

22. The method of claim 16 wherein the condition is anorexia nervosa or bulimia nervosa.

23. The method of claim 16 wherein the condition is premature ejaculation.

24. A method of blocking the reuptake of serotonin in a subject comprising providing to the subject an effective amount of a compound of claim 1.

25. A method of agonizing the $5HT_{1A}$ receptor in a subject comprising providing to the subject an effective amount of a compound of claim 1.

26. A method comprising contacting a $5HT_{1A}$ receptor with a compound of claim 1.

* * * * *